US009195075B2

(12) United States Patent
Pugh et al.

(10) Patent No.: US 9,195,075 B2
(45) Date of Patent: Nov. 24, 2015

(54) FULL RINGS FOR A FUNCTIONALIZED LAYER INSERT OF AN OPHTHALMIC LENS

(75) Inventors: Randall B. Pugh, Jacksonville, FL (US); Frederick A. Flitsch, New Windsor, NY (US); Daniel B. Otts, Fruit Cove, FL (US); James D. Riall, St. Johns, FL (US); Adam Toner, Jacksonville, FL (US)

(73) Assignee: Johnson & Johnson Vision Care, Inc., Jacksonville, FL (US)

(*) Notice: Subject to any disclaimer, the term of this patent is extended or adjusted under 35 U.S.C. 154(b) by 280 days.

(21) Appl. No.: 13/402,255

(22) Filed: Feb. 22, 2012

(65) Prior Publication Data
US 2013/0215377 A1 Aug. 22, 2013
US 2015/0077702 A9 Mar. 19, 2015

Related U.S. Application Data

(63) Continuation-in-part of application No. 13/401,959, filed on Feb. 22, 2012.

(60) Provisional application No. 61/454,591, filed on Mar. 21, 2011.

(51) Int. Cl.
*G02C 7/02* (2006.01)
*G02C 7/08* (2006.01)
*B29D 11/00* (2006.01)
*G02C 7/10* (2006.01)

(52) U.S. Cl.
CPC .......... *G02C 7/083* (2013.01); *B29D 11/00817* (2013.01); *G02C 7/02* (2013.01); *G02C 7/101* (2013.01)

(58) Field of Classification Search
CPC ...... G02C 7/083; G02C 7/101; A61F 2/1624; A61F 2/1627; A61F 2/1629; A61F 2/1632; A61F 2/1635
USPC ........................................ 351/159.39, 159.03
See application file for complete search history.

(56) References Cited

U.S. PATENT DOCUMENTS

| 4,601,545 | A | 7/1986 | Kern |
| 6,322,589 | B1 | 11/2001 | Cumming |
| 7,404,636 | B2* | 7/2008 | Blum et al. .............. 351/159.03 |
| 7,410,700 | B2 | 8/2008 | Wang |
| 7,798,301 | B2 | 9/2010 | Keating et al. |
| 8,343,216 | B2 | 1/2013 | Brady et al. |

(Continued)

FOREIGN PATENT DOCUMENTS

| EP | 1760515 A2 | 3/2007 |
| WO | WO 2007/050402 A2 | 5/2007 |

(Continued)

OTHER PUBLICATIONS

PCT International Search Report, dated Oct. 2, 2012 for PCT Int'l Appln. No. PCT/US2012/029796.

(Continued)

*Primary Examiner* — Jordan Schwartz (57) ABSTRACT

This invention discloses various designs for rings that make up the functionalized layers in a functional layer insert. More specifically, design parameters for the rings for incorporation into an ophthalmic lens. Additionally, functional aspects of the rings and materials for encapsulating the functional insert into an area outside the optical zone of the ophthalmic lens.

19 Claims, 6 Drawing Sheets

(56) References Cited

U.S. PATENT DOCUMENTS

| | | | |
|---|---|---|---|
| 8,579,435 B2* | 11/2013 | Blum et al. | 351/159.39 |
| 8,950,862 B2 | 2/2015 | Pugh et al. | |
| 2004/0131925 A1 | 7/2004 | Jenson et al. | |
| 2005/0099594 A1 | 5/2005 | Blum et al. | |
| 2006/0095128 A1* | 5/2006 | Blum et al. | 623/6.37 |
| 2006/0265058 A1 | 11/2006 | Sivestrini | |
| 2007/0242173 A1 | 10/2007 | Blum et al. | |
| 2008/0208335 A1 | 8/2008 | Blum et al. | |
| 2009/0091818 A1 | 4/2009 | Haddock et al. | |
| 2009/0204207 A1* | 8/2009 | Blum et al. | 623/4.1 |
| 2009/0244477 A1 | 10/2009 | Pugh et al. | |
| 2009/0256977 A1 | 10/2009 | Haddock et al. | |
| 2010/0001926 A1 | 1/2010 | Amirparviz et al. | |
| 2010/0002190 A1 | 1/2010 | Clarke et al. | |
| 2010/0072643 A1 | 3/2010 | Pugh et al. | |
| 2010/0073534 A1 | 3/2010 | Yano et al. | |
| 2010/0076553 A1 | 3/2010 | Pugh et al. | |
| 2010/0078838 A1* | 4/2010 | Pugh et al. | 264/1.38 |
| 2010/0109175 A1 | 5/2010 | Pugh et al. | |
| 2010/0110372 A1 | 5/2010 | Pugh et al. | |
| 2011/0045112 A1 | 2/2011 | Pugh et al. | |
| 2011/0230963 A1 | 9/2011 | Cuevas | |
| 2012/0236254 A1 | 9/2012 | Pugh et al. | |
| 2012/0245444 A1 | 9/2012 | Otis et al. | |
| 2013/0194540 A1* | 8/2013 | Pugh et al. | 351/159.03 |
| 2013/0245754 A1 | 9/2013 | Blum et al. | |
| 2013/0245755 A1 | 9/2013 | Fehr et al. | |
| 2014/0036226 A1 | 2/2014 | Blum et al. | |
| 2014/0148899 A1 | 5/2014 | Fehr et al. | |
| 2014/0306361 A1 | 10/2014 | Pugh et al. | |

FOREIGN PATENT DOCUMENTS

| | | | |
|---|---|---|---|
| WO | WO 2010/051225 A1 | 5/2010 | |
| WO | WO 2011/163080 A1 | 12/2011 | |

OTHER PUBLICATIONS

European Search Report for Application No. EP 13 15 5410 Date of Completion of Report Jun. 5, 2013.

* cited by examiner

FULL RINGS FOR A FUNCTIONALIZED LAYER INSERT OF AN OPHTHALMIC LENS

CROSS REFERENCE TO RELATED APPLICATIONS

The present application claims priority as a Continuation in Part Application to U.S. patent application No. 13/401,959 filed Feb. 22, 2012, and entitled, "Methods and Apparatus for Functional Insert with Power Layer," which claims priority to U.S. Provisional Application No. 61/454,591, filed Mar. 21, 2011, and entitled, "Methods and Apparatus for Functional Insert with Power Layer." The contents of these applications are relied upon and incorporated herein by reference.

FIELD OF USE

This invention describes a functionalized layer insert for an ophthalmic device formed from multiple functional layers which are stacked. More specifically, various designs for full rings that comprise the functional layers.

BACKGROUND

Traditionally an ophthalmic device, such as a contact lens, an intraocular lens or a punctal plug included a biocompatible device with a corrective, cosmetic or therapeutic quality. A contact lens, for example, can provide one or more of: vision correcting functionality; cosmetic enhancement; and therapeutic effects. Each function is provided by a physical characteristic of the lens. A design incorporating a refractive quality into a lens can provide a vision corrective function. A pigment incorporated into the lens can provide a cosmetic enhancement. An active agent incorporated into a lens can provide a therapeutic functionality. Such physical characteristics are accomplished without the lens entering into an energized state. A punctal plug has traditionally been a passive device.

More recently, it has been theorized that active components may be incorporated into a contact lens. Some components can include semiconductor devices. Some examples have shown semiconductor devices embedded in a contact lens placed upon animal eyes. It has also been described how the active components may be energized and activated in numerous manners within the lens structure itself. The topology and size of the space defined by the lens structure creates a novel and challenging environment for the definition of various functionalities. Generally, such disclosures have included discrete devices. However, the size and power requirements for available discrete devices are not necessarily conducive for inclusion in a device to be worn on a human eye.

SUMMARY

Accordingly, the present invention includes a functionalized layer insert that can be energized and incorporated into an ophthalmic device. The insert can be formed of multiple layers which may have unique functionality for each layer; or alternatively mixed functionality but in multiple layers. The layers may in some embodiments have layers dedicated to the energization of the product or the activation of the product or for control of functional components within the lens body.

In some embodiments, the functionalized layer insert may contain a layer in an energized state which is capable of powering a component capable of drawing a current. Components may include, for example, one or more of: a variable optic lens element, and a semiconductor device, which may either be located in the stacked layer insert or otherwise connected to it. Some embodiments can also include a cast molded silicone hydrogel contact lens with a rigid or formable insert of stacked functionalized layers contained within the ophthalmic lens in a biocompatible fashion.

Accordingly, the present invention includes a disclosure of an ophthalmic lens with a stacked functionalized layer portion as well as various designs for rings that comprise the functional layers. Full ring designs parameters can include, for example, thickness, shape, stacking structure, etc. In some embodiments, design parameters may be influenced by one or more of; the thickness around an optical zone of the lens, the base curve of the lens, the diameter of the lens and encapsulation parameters.

An insert may be formed from multiple layers in various manners and placed in proximity to one, or both of, a first mold part and a second mold part. A reactive monomer mix is placed between the first mold part and the second mold part. The first mold part is positioned proximate to the second mold part thereby forming a lens cavity with the energized substrate insert and at least some of the reactive monomer mix in the lens cavity; the reactive monomer mix is exposed to actinic radiation to form an ophthalmic lens. Lenses may be formed via the control of actinic radiation to which the reactive monomer mixture is exposed.

DETAILED DESCRIPTION OF THE INVENTION

The present invention includes a substrate insert device formed through the stacking of multiple functionalized layers. Additionally the present invention includes various designs for a wafer including rings that may be used to make up functionalized layers in a functional layer insert, for incorporation into an ophthalmic lens.

In the following sections detailed descriptions of embodiments of the invention will be given. The description of both preferred and alternative embodiments are exemplary embodiments only, and it is understood that to those skilled in the art that variations, modifications and alterations may be apparent. It is therefore to be understood that said exemplary embodiments do not limit the scope of the underlying invention.

Glossary

In this description and claims directed to the presented invention, various terms may be used for which the following definitions will apply:

Active Lens Insert: as used herein refers to an electronic or electromechanical device with controls based upon logic circuits.

Arc-matched (or arc matching): as used herein refers to the design of a Ring Segment which includes an identical External Radius and Internal Radius, such that the curvature of the External Arc matches the curvature of the Internal Arc. Arc matching is used to efficiently nest Ring Segments on a Wafer, maximizing wafer utilization.

Dicing Street Width: as used herein refers to the width of a thin non-functional space between integrated circuits on a Wafer, where a saw or other device or method can safely cut the Wafer into individual Die without damaging the circuits.

Die: as used herein refers to a block of semiconducting material, on which a given functional circuit is fabricated. Die are created on and cut from a Wafer.

Energized: as used herein refers to the state of being able to supply electrical current to or to have electrical energy stored within.

Energy: as used herein refers to the capacity of a physical system to do work. Many uses within this invention may relate to the said capacity being able to perform electrical actions in doing work.

Energy Source: as used herein refers to device capable of supplying Energy or placing a biomedical device in an Energized state.

External Arc: as used herein refers to the external or convex edge of a Ring Segment, which is a portion of the circumference of the circle defined by the External Radius.

External Radius: as used herein refers to the radius of the circle that defines the external edge of a Full Ring or Ring Segment. The External Radius determines the curvature of the External Arc.

Full Ring: as used herein refers to one complete ring-shaped layer in a Functionalized Layer Insert. A Full Ring may be comprised of multiple Ring Segments or may be one Intact Ring.

Functionalized: as used herein refers to making a layer or device able to perform a function including for example, energization, activation, or control.

Functionalized Layer Insert: as used herein refers to an insert for an ophthalmic device formed from multiple functional layers which are stacked. The multiple layers may have unique functionality for each layer; or alternatively mixed functionality but in multiple layers. In some preferred embodiments, the layers are rings.

Intact Ring: as used herein refers to one complete ring-shaped layer in a Functionalized Layer Insert which is made of a single intact Die.

Internal Arc: as used herein refers to the internal or concave edge of a Ring Segment. The Internal Arc may, in some embodiments, be a single arc segment, the curvature of which is determined by the Internal Radius. In other embodiments the Internal Arc may be comprised of multiple arc segments of different curvatures, defined by different Internal Radii.

Internal Radius: as used herein refers to the radius of the circle that defines the internal edge or a portion of the internal edge of a Full Ring or Ring Segment. The Internal Radius determines the curvature of the Internal Arc.

Lens: refers to any ophthalmic device that resides in or on the eye. These devices can provide optical correction or may be cosmetic. For example, the term lens can refer to a contact lens, intraocular lens, overlay lens, ocular insert, optical insert or other similar device through which vision is corrected or modified, or through which eye physiology is cosmetically enhanced (e.g. iris color) without impeding vision. In some embodiments, the preferred lenses of the invention are soft contact lenses are made from silicone elastomers or hydrogels, which include but are not limited to silicone hydrogels, and fluorohydrogels.

Mold: refers to a rigid or semi-rigid object that may be used to form lenses from uncured formulations. Some preferred molds include two mold parts forming a front curve mold part and a back curve mold part.

Power: as used herein refers to work done or energy transferred per unit of time.

Ring Segment: as used herein refers to one Die which may be combined with other Die to construct a Full Ring. As used in this invention, a Ring Segment is generally flat and is formed in an arcuate shape.

Stacked: as used herein means to place at least two component layers in proximity to each other such that at least a portion of one surface of one of the layers contacts a first surface of a second layer. In some embodiments, a film, whether for adhesion or other functions may reside between the two layers that are in contact with each other through said film.

Substrate insert: as used herein refers to a formable or rigid substrate capable of supporting an Energy Source within an ophthalmic lens. In some embodiments, the Substrate insert also supports one or more components.

Wafer: as used herein refers to a thin slice of semiconductor material, such as silicon crystal, used in the fabrication of integrated circuits and other microdevices. The wafer serves as the substrate for microelectronic devices built in and over the wafer and undergoes many microfabrication process steps.

Apparatus

Figure 1:
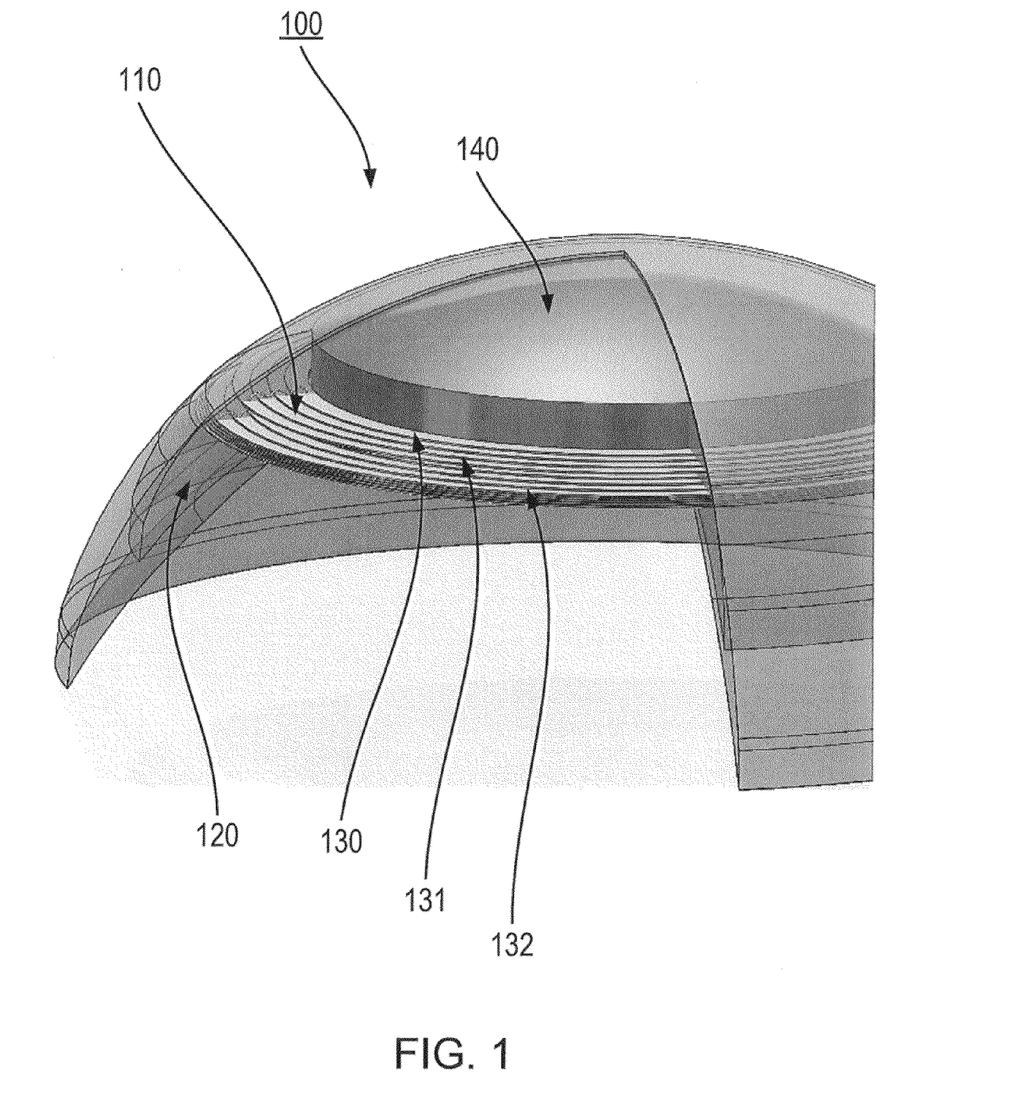
FIG. 1 illustrates a three dimensional section representation of an insert formed of stacked functional layers which is incorporated within an ophthalmic lens mold part.

Referring now to FIG. 1, demonstrated as item 100 is a three dimensional representation of some embodiments of a fully formed ophthalmic lens using a stacked layer substrate insert formed as a functionalized layer insert 110. The representation shows a partial cut out from the ophthalmic lens to realize the different layers present inside the device. A body material 120 is shown in cross section of the encapsulating layers of the substrate insert. The body material 120 is contained fully within and extends around the entire circumference of the ophthalmic lens. It may be clear to one skilled in the arts that the actual functionalize layer insert 110 may comprise a full annular ring or other shapes that still may reside within the constraints of the size of a typical ophthalmic lens.

Layers 130, 131 and 132 illustrate three of numerous layers that may be found in a functionalized layer insert 110. In some embodiments, a single layer may include one or more of: active and passive components and portions with structural, electrical or physical properties conducive to a particular purpose.

In some embodiments, a layer 130 may include an energization source, such as, for example, one or more of: a battery, a capacitor and a receiver within the layer 130. Item 131 then, in a non limiting exemplary sense, may comprise microcircuitry in a layer that detects actuation signals for an active lens insert 140. In some embodiments, a power regulation layer 132, may be included that is capable of receiving power from external sources, charging the battery layer 130 and controlling the use of battery power from layer 130 when the lens is not in a charging environment. The power regulation layer 132 may also control signals to an exemplary active lens insert 140 in the center annular cutout of the functionalized layer insert 110.

In general, according to this embodiment, a functionalized layer insert 110 is embodied within an ophthalmic lens via automation which places an energy source a desired location relative to a mold part used to fashion the lens.

Figure 2:
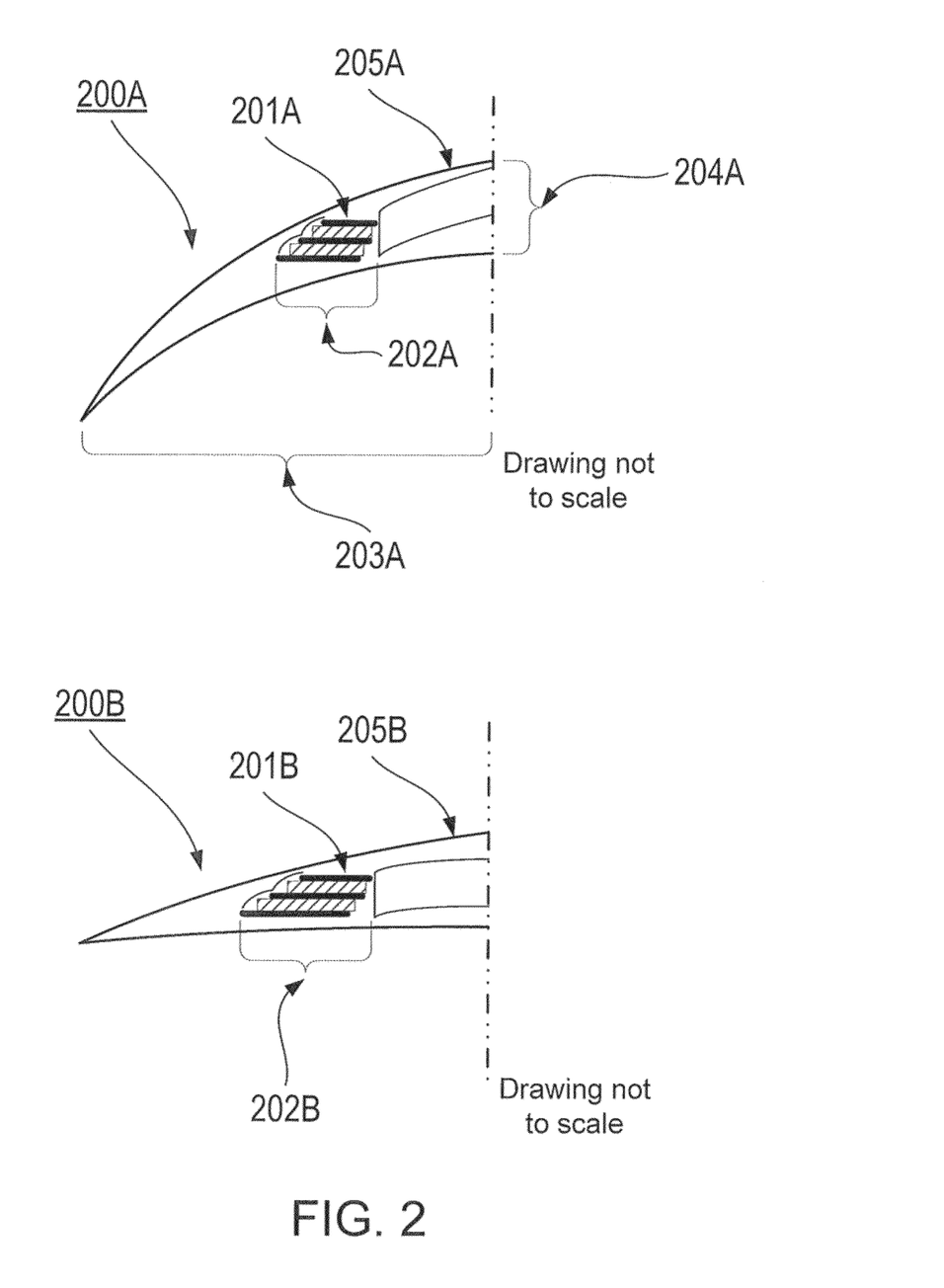
FIG. 2 illustrates two cross-sectional representations of inserts formed of stacked functional layers incorporated within two different shaped ophthalmic lenses.
Figure 3:
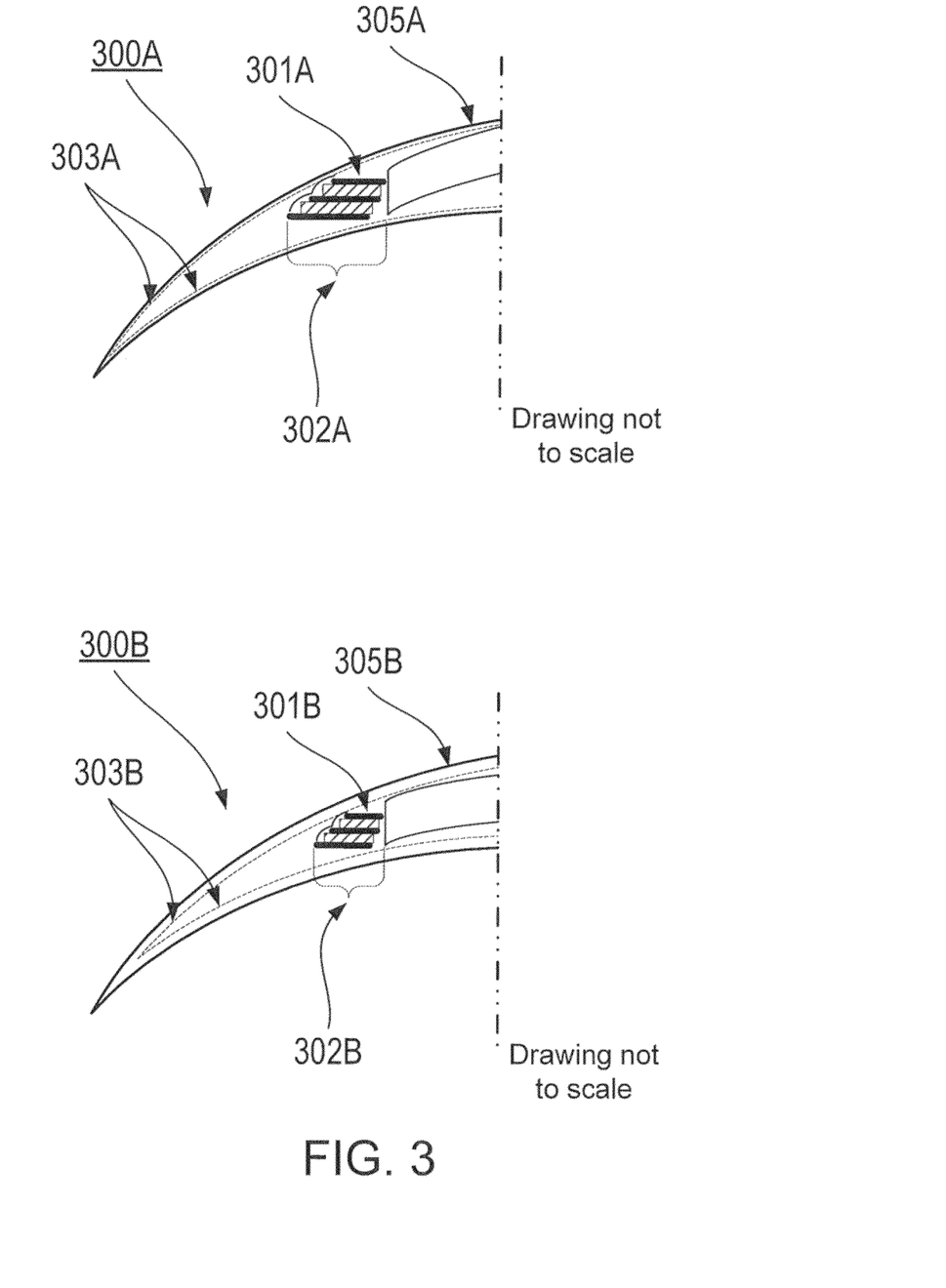
FIG. 3 illustrates two cross-sectional representations of inserts formed of stacked functional layers incorporated within ophthalmic lenses with different encapsulation parameters.
Figure 4:
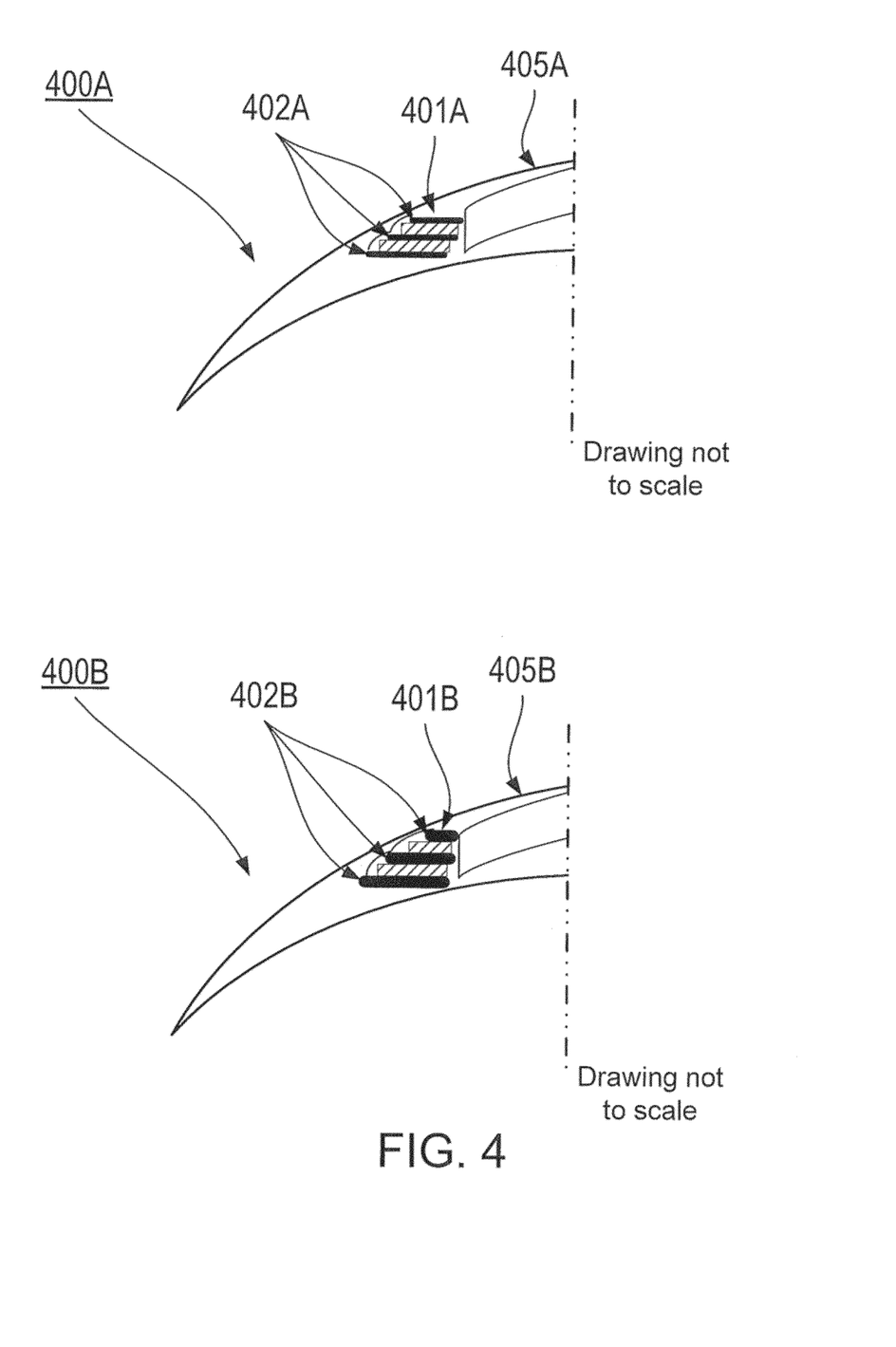
FIG. 4 illustrates two cross-sectional representations of inserts formed of stacked functional layers with different layer thicknesses incorporated within ophthalmic lenses.

The size, shape, and stacking structure of the die that may be used to form layers such as 130, 131 and 132 in a functionalized layer insert 110 is influenced by several factors, as shown in FIGS. 2, 3 and 4.

FIG. 2 illustrates the effect of lens shape on the design of a functionalized layer insert. The base curve, diameter, and thickness of an ophthalmic lens define a maximum size and shape of an included functionalized layer insert. FIG. 2 shows, as one example, the impact of different base curves. Item 200A depicts a cross sectional view of a portion of an ophthalmic lens 205A with more curvature than the ophthalmic lens 205B, depicted in item 200B, which is flatter. The flatter lens 205B can accommodate a functionalized layer insert 201B of greater width 202B, as compared to the narrower width 202A of a functionalized layer insert 201A that fits within lens 205A having greater base curvature. It should be apparent that a lens of smaller diameter (203A indicates a lens diameter) would limit the width of a functionalized layer insert while a lens with larger diameter would accommodate a wider functionalized layer insert. Likewise, a lens of less thickness (204A indicates a lens thickness) would limit the number of layers in a functionalized layer insert as well as the width of a functionalized layer insert, while a thicker lens might support more layers and layers of greater width. Lens thickness 204A in this embodiment is measured in and around the optic zone.

FIG. 3 illustrates the effect of encapsulation parameters on the design of a functionalized layer insert. Encapsulation parameters, such as, by way of non-limiting example, maintaining a minimum 100 micron thickness between the edge of a die and the outer edge of a lens, affect the size and shape of a functionalized layer insert and therefore the size and shape of individual layers. Item 300A depicts a cross-sectional view of a portion of an ophthalmic lens 305A with a functionalized layer insert 301A and encapsulation boundary 303A. The ophthalmic lens 305B depicted in item 300B includes a functionalized layer insert 301B and a relatively wider encapsulation boundary 303B as compared to boundary 303A which is narrower. It can be seen that the wider encapsulation boundary 303B necessitates that the functionalized layer insert 301B be narrower in width 302B as compared to the functionalized layer insert 301A with width 302A.

Depicted in FIG. 4 is the effect of functional layer thickness on the design of a functionalized layer insert. Item 400A represents a cross-sectional view of a portion of an ophthalmic lens 405A with a functionalized layer insert 401A including three layers with material, such as, for example, insulating layers, between the functional layers. A functionalized layer insert may contain more or less than three layers. The ophthalmic lens 405B depicted in item 400B includes a functionalized layer insert 401B with relatively thicker layers 402B as compared to the layers 402A in the functionalized layer insert 401A which are thinner. The lens curvature in these two examples allows the width of the bottom layers 402A and 402B to remain the same. However, it can be seen that the increased height of the functionalized layer insert 401B as compared to 401A, combined with the lens curvature, causes the top layer 402A to be limited in width. The thickness of each functional layer impacts other dimensions, such as functional layer width, that will fit within the required lens and encapsulation parameters. Thicker layers within the functionalized layer insert will be more restricted in other dimensions, such as width, in order to remain within the confines of the lens geometry.

The embodiment depicted in this invention includes a functionalized layer insert in the shape of a ring, formed as an intact ring-shaped die.

Full Ring Layout

Figure 5A:
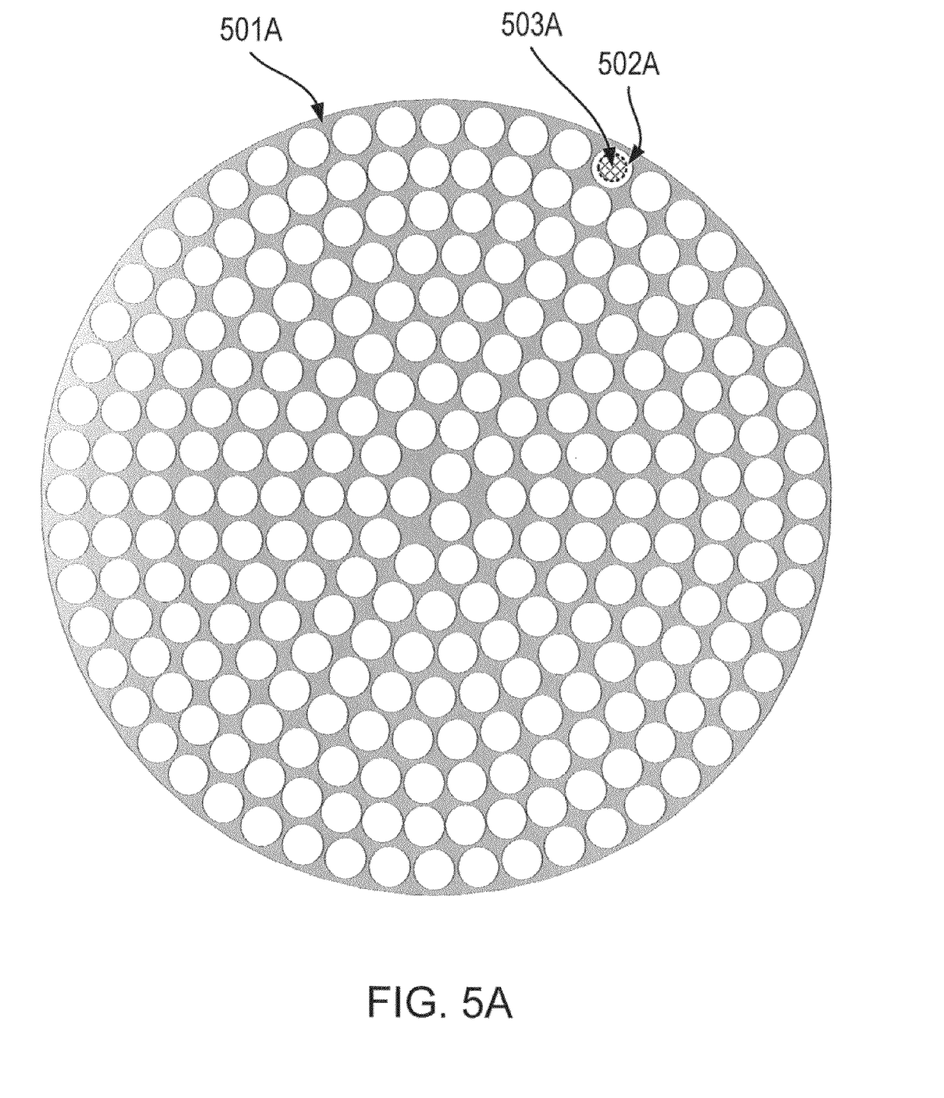
FIG. 5A illustrates a top-down view of a wafer with an arrangement of full annular die according to some embodiments of the present invention.

Referring now to FIG. 5A, depicted is a top-down view of an 8-inch wafer 501A with a layout including full ring die 502A with center cutout 503A. The figure shows the area required for each full ring die 502A, but only illustrates an example of the center cutout 503A for one full ring die 502A. Full ring die 502A are positioned adjacent to one another, with at least a dicing street width separation between rings. The most efficient layout includes full ring die 502A arranged in concentric circles around the circumference of the wafer. In this design, significant areas between the individual full ring die 502A are not usable, as well as the center cutout 503A portion of each ring. A layout including full ring die 501A results in inefficient utilization of a wafer, producing 255 full rings and utilizing only 25.9% of the wafer material.

Figure 5B:
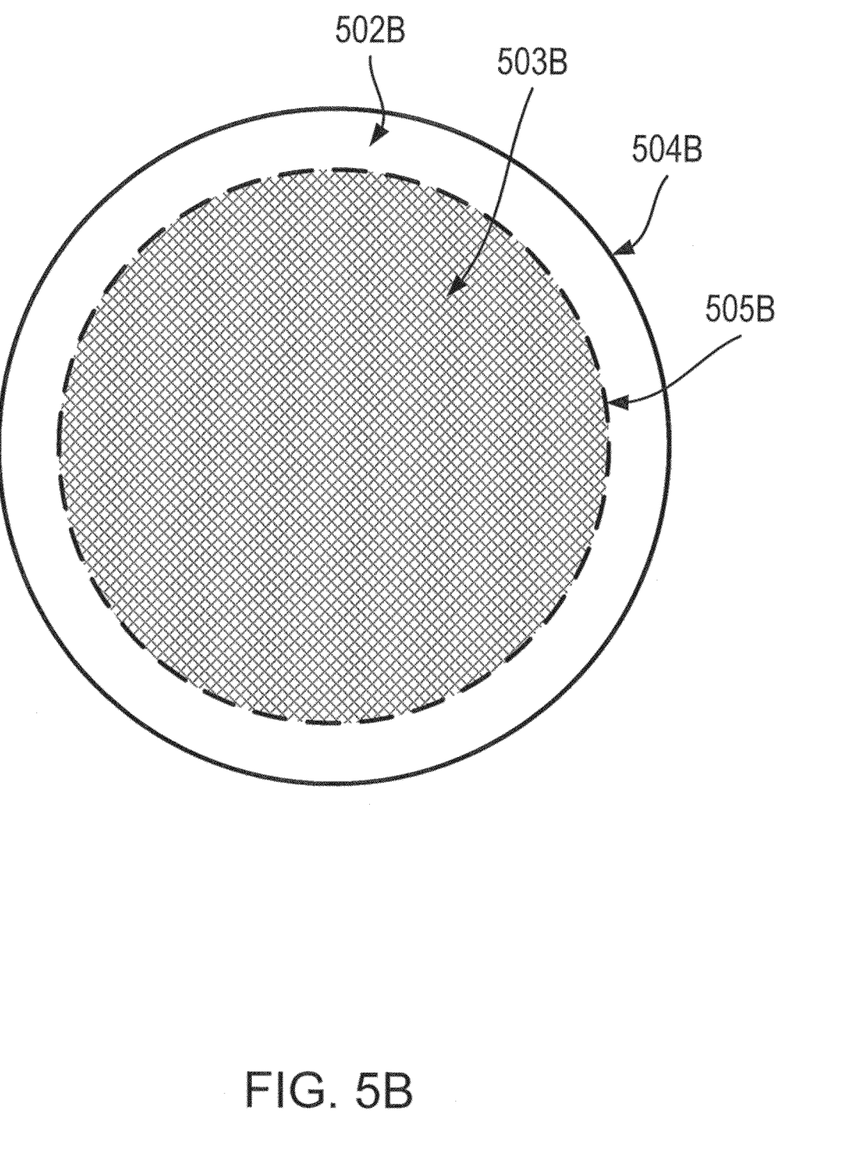
FIG. 5B illustrates a top-down close up view of one full annular die with center cutout according to some embodiments of the present invention.

Referring now to FIG. 5B, a top-down close up view of a full ring die 502B is depicted with center cutout 503B. When the center cutout 503B is removed, the full ring die 502B is defined by an outer perimeter 504B and an inner perimeter 505B. The center cutout 503B is unusable after removal from each full ring die 502B produced on a wafer, and is therefore wasted material.

Conclusion

The present invention, as described above and as further defined by the claims below, provides various designs for rings that make up the functionalized layers in a functional layer insert, for incorporation into an ophthalmic lens.

The invention claim is:

1. An active lens insert for an ophthalmic lens comprising:
    a stacked composite structure comprising: annular shaped full ring substrate layers with one or both of electrical and logical functionality; and
    electrical interconnections between the annular shaped full ring substrate layers to create the active lens insert;
    wherein each of the annular shaped full ring substrate layers have a different radius and encircle an optical zone of the ophthalmic lens; and
    wherein a size and a stacking structure of the annular shaped full ring substrate layers are selected to allow encapsulation of the active lens insert in a region around an optical zone of the ophthalmic lens.

2. The active lens insert of claim 1, wherein the annular shaped full ring substrate layers are adhered to insulating layers forming the stacked composite structure.

3. The active lens insert of claim 1, wherein the annular shaped full ring substrate layers are cut from a wafer.

4. The active lens insert of claim 1, wherein the size and the stacking structure for the annular shaped full ring substrate layers is further based on a base curve of the ophthalmic lens.

5. The active lens insert of claim 1, wherein the size and the stacking structure for the annular shaped full ring substrate layers is further based on a diameter of the ophthalmic lens.

6. The active lens insert of claim 1, wherein the size and the stacking structure for the annular shaped full ring substrate layers is further based on encapsulation parameters of the ophthalmic lens.

7. The active lens insert of claim 1, wherein the active lens insert comprises at least three annular shaped full ring substrate layers.

8. The active lens insert of claim 1, wherein the active lens insert comprises a full ring annular shape.

9. The active lens insert of claim 7, wherein at least one of the annular shaped full ring substrate layers comprises a metallic layer configured to act as an antenna.

10. The active lens insert of claim 7, wherein at least one of the annular shaped full ring substrate layers of the active lens insert comprises an energization source.

11. The active lens insert of claim 7, wherein at least one of the annular shaped full ring substrate layers of the active lens insert comprises a power regulation source.

12. The active lens insert of claim 11, wherein the power regulation source comprises at least one semiconductor layer with electronic microcircuitry capable to control electric current flow from electrochemical cells.

13. The active lens insert of claim 12, wherein the electronic microcircuitry is electrically connected to an electroactive lens component within the ophthalmic lens.

14. The active lens insert of claim 12, wherein the power regulation source is capable of receiving power from external sources.

15. The active lens insert of claim 12, wherein the power regulation source is capable of charging a battery layer.

16. The active lens insert of claim 12, wherein the power regulation source is capable of controlling the use of power when the ophthalmic lens is not in a charging environment.

17. The active lens insert of claim 12, wherein the power regulation source is capable of controlling the use of power when the ophthalmic lens is in a charging environment.

18. The active lens insert of claim 12, wherein at least one of the annular shaped full ring substrate layers of the active lens insert comprises a solid state energy source.

19. The active lens insert of claim 1, wherein at least one of the annular shaped full ring substrate layers comprises microcircuitry to detect actuation signals for the active lens insert.

* * * * *